United States Patent [19]

O'Brien et al.

[11] Patent Number: 6,156,097
[45] Date of Patent: Dec. 5, 2000

[54] CO₂ REMOVABLE FROM FLUOROCARBONS BY SEMIPERMEABLE MEMBRANE

[75] Inventors: William G. O'Brien, Newark; Charles J. Noelke, Wilmington, both of Del.; Raymond C. Harker, Williamstown, N.J.; David John Van Bramer, Belpre, Ohio

[73] Assignee: E. I. du Pont de Nemours and Company, Wilmington, Del.

[21] Appl. No.: 09/070,904

[22] Filed: May 1, 1998

Related U.S. Application Data

[60] Provisional application No. 60/044,013, May 2, 1997.

[51] Int. Cl.⁷ .................................................. B01D 53/22
[52] U.S. Cl. ..................................................... 95/51; 95/45
[58] Field of Search ..................................... 95/45, 51, 50

[56] References Cited

U.S. PATENT DOCUMENTS

| | | | |
|---|---|---|---|
| 4,879,396 | 11/1989 | Ozero | 549/534 |
| 4,990,168 | 2/1991 | Sauer et al. | 95/51 X |
| 5,042,992 | 8/1991 | Blinka et al. | 55/16 |
| 5,067,970 | 11/1991 | Wang et al. | 95/51 |
| 5,076,817 | 12/1991 | Hayes | 95/51 X |
| 5,085,676 | 2/1992 | Ekiner et al. | 55/158 |
| 5,085,774 | 2/1992 | Ekiner | 210/500.23 |
| 5,105,270 | 4/1992 | Takahashi et al. | 358/113 |
| 5,120,329 | 6/1992 | Sauer et al. | 55/16 |
| 5,233,837 | 8/1993 | Callahan | 95/51 X |
| 5,234,471 | 8/1993 | Weinberg | 95/51 X |
| 5,345,013 | 9/1994 | Bramer et al. | 570/102 |
| 5,411,721 | 5/1995 | Doshi et al. | 95/51 X |
| 5,482,539 | 1/1996 | Callahan | 95/51 |
| 5,534,151 | 7/1996 | Lee | 95/45 X |
| 5,591,250 | 1/1997 | Stern et al. | 95/51 |
| 5,618,332 | 4/1997 | Ekiner et al. | 95/51 |
| 5,674,957 | 10/1997 | Desimone et al. | 526/89 |
| 5,702,503 | 12/1997 | Tse Tang | 95/51 X |
| 5,709,733 | 1/1998 | Hachisuka et al. | 95/51 |
| 5,730,779 | 3/1998 | Chernyakov et al. | 95/45 |
| 5,759,237 | 6/1998 | Li et al. | 95/45 X |
| 5,814,127 | 9/1998 | Li | 95/51 X |
| 5,855,647 | 1/1999 | Li et al. | 95/51 X |
| 5,858,065 | 1/1999 | Li et al. | 95/45 |
| 5,858,066 | 1/1999 | O'Brien et al. | 95/45 X |

FOREIGN PATENT DOCUMENTS

| | | |
|---|---|---|
| 0 128 506 | 12/1984 | European Pat. Off. . |
| 0 200 518 | 11/1986 | European Pat. Off. . |
| 0 373 683 | 6/1990 | European Pat. Off. . |
| 0 501 933 A2 | 2/1992 | European Pat. Off. . |
| 6-116180 | 10/1992 | Japan . |
| WO95/32169 | 11/1995 | WIPO . |

OTHER PUBLICATIONS

Membranes can Efficiently Separate CO₂ From Mixtures, Schell et al., Oil & Gas Journal, Aug. 15, 1983, p. 83.

Relationship Between Gas Separation Properties and Chemical Structure in a Series of Aromatic Polyimides, Kim et al., Journal of Membrane Science, 37 (1988), 45–62.

*Primary Examiner*—Robert H. Spitzer

[57] ABSTRACT

A process for removing carbon dioxide from a fluorocarbon carbon dioxide mixture in which the fluorocarbon carbon dioxide mixture is contacted with a semipermeable polyimide membrane to form at least one exit stream having an increased concentration of carbon dioxide and at least one exit stream having a reduced concentration of carbon dioxide.

12 Claims, 2 Drawing Sheets

CO₂ REMOVABLE FROM FLUOROCARBONS BY SEMIPERMEABLE MEMBRANE

RELATED APPLICATIONS

This application claims the benefit of U.S. Provisional Application No. 60/044,013, filed May 2, 1997.

FIELD OF THE INVENTION

This invention relates to a process for removing quantities of carbon dioxide from fluorocarbons.

BACKGROUND OF THE INVENTION

Conventional methods of manufacturing and purifying non-chlorine-containing fluorocarbons typically result in a product containing at least a small amount of undesired impurities. These fluorocarbons are useful as refrigerants, blowing agents, cleaning agents and many other applications. When any of these compounds are used as an etchant in electronics applications, purity requirements are unusually high. Even trace impurities can markedly affect the reject rate for miniaturized electronic circuits or optical disks, in some cases affecting the reject rate a thousand-fold. As a result, highly purified fluorocarbons used for such applications typically require unusually stringent purification procedures and command a premium market position and price. Two of the compounds so used are trifluoromethane (HFC-23) and hexafluoroethane (FC-116).

It is known that HFC-23 can be made in a mixture with chlorofluoromethanes by intensive fluorination of chloromethane compounds under special conditions, or by disproportionation of chlorodifluoromethane (HCFC-22). These reactions are costly to carry out on a small scale because of the small volume of HFC-23 required, and the reaction products require extensive purification to obtain a product of sufficient purity for the etchant market.

It is also known that commercial processes to make the important refrigerant chlorodifluoromethane (HCFC-22) on a large scale by catalytic reaction of chloroform with HF typically also produce several percent of HFC-23 as a byproduct. Depending on the size and design of the plant, this HFC-23 can be vented to the atmosphere or recovered. The environmentally desirable recovery of HFC-23 for sale to the etchant market is costly because of the small percentage produced and the number of impurities which must be removed.

It is also known that FC-116 can be made by similar catalytic processes involving the reaction of HF or fluorine with perchloroethylene or other two-carbon halocarbons. Again, these processes yield a product that requires extensive purification for the etchant market.

Other fluorocarbons such as perfluoroepoxides are useful in preparation of various fluoropolymers. One of the most important perfluoroepoxides is hexafluoropropylene oxide, or HFPO, which is used to make a variety of specialty fluorochemical polymers with complex structures. The presence of small amounts of impurities interferes with many of the subsequent processing steps, particularly in polymerization, where low levels of impurities can have a serious limiting effect on achieving the desired molecular weight polymer. Hexafluoropropylene oxide (HFPO) is typically manufactured by oxidation of hexafluoropropylene (HFP) using oxidizing agents such as hydrogen peroxide, sodium hypochlorite, oxygen or ozone.

Most of the bulk impurities from the above reactions to make HFC-23, FC-116 or HFPO can be readily removed from the desired fluorocarbon by careful fractional distillation and/or scrubbing to remove acids, followed by drying by passing through a silica gel bed. When HFPO is manufactured by oxidation of HFP, HFP can be present in the stream to be purified but would usually not be considered to be an impurity. However, even after careful purification, these compounds typically contain small amounts of carbon dioxide ($CO_2$). This may result from the presence of $CO_2$ in the water used for scrubbing acidic impurities, as a byproduct of the reaction, or from other sources. For generally non-reactive fluorocarbons such as HFC-23 and FC-116, the amount of $CO_2$ can be reduced by scrubbing the fluorocarbon with an excess of caustic solution (relative to the $CO_2$), or by passing it through a fixed bed of soda-lime pellets, also present in excess relative to the amount of $CO_2$. The reactions involved are shown below:

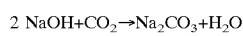

$$2\ NaOH + CO_2 \rightarrow Na_2CO_3 + H_2O$$

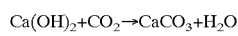

$$Ca(OH)_2 + CO_2 \rightarrow CaCO_3 + H_2O$$

However it is difficult to achieve reliably low levels of $CO_2$ with either of these approaches because the needed excess of alkali results in an alkali-alkali carbonate mixture, the composition of which must be carefully and continually monitored for maximum effective removal of the $CO_2$. That is, if the proportion of alkali carbonate in the resulting alkali-alkali carbonate mixture becomes too high, the mixture becomes less effective in removing $CO_2$, and the product no longer meets specifications [a current goal is 50 parts per million (ppm) of $CO_2$ on a molecular or volume basis, with a future goal of 10 ppm]. If the alkali-alkali carbonate mixture is replaced with fresh alkali while the proportion of alkali carbonate is too low, the cost of the operation becomes excessive. In addition, either approach creates an alkali-alkali carbonate mixture which must be disposed of. Furthermore, either of these steps introduces some water (from the scrubbing solution and/or as neutralization byproduct) into the dry fluorocarbon which must then be removed in an additional step.

For more reactive fluorocarbons such as HFPO, scrubbing with an alkali may give rise to unwanted side reactions and yield losses.

Processes have been proposed for removing trace quantities of impurities from etchant gases by contacting them at high temperatures with special Zr-V-Fe alloys as disclosed in EP 501 933 A2, or by contacting with hydrogenated Ni-NiO catalysts as disclosed in JP 06116180 A2, in order to react with and remove the impurities. These methods of treatment are costly.

It is also known to carry out polymerizations of fluorinated monomers in media comprising $CO_2$. See, for example, U.S. Pat. No. 5,674,957. Unreacted monomers from such processes are desirably recovered from mixtures with $CO_2$ for recycle to the polymerization reaction.

There is a need for a process to remove low or trace quantities of $CO_2$ from fluorocarbons such as HFC-23, FC-116 or HFPO in a reliable manner without contacting them with other chemicals which can introduce water or other impurities and create waste disposal problems or problems in polymerization for polymerizable monomers, or require costly alloy or catalyst reaction treatments.

DESCRIPTION OF THE RELATED ART

The use of semipermeable membranes to separate gases other than $CO_2$ and fluorocarbons is well known. Many of the separations disclosed in the literature are based on polyimide membranes. For example, Kim et al., "Relationship between Gas Separation Properties and Chemical Structure in a Series of Aromatic Polyimides", Journal of Membrane Science, 37 (1988), 45–62, discloses various polyimide structures tested for a number of gas separations.

Many other such references describe polyimide structures for gas permeation. U.S. Pat. No. 5,015,270 discloses a process for separation of gases using a polyimide membrane having phenylindane residues incorporated in the polyimide backbone chain. A preferred polyimide is "MATRIMID" 5218 polyimide resin, made by Ciba-Geigy and based on 5(6)-amino-1-(4'-aminophenyl)-1,3-trimethylindane. Examples to demonstrate selectivity were made with common atmospheric gases ($O_2$, $N_2$, $CO_2$, He).

U.S. Pat. No. 5,085,676 discloses a process for preparing a multicomponent membrane comprising a porous polymeric substrate and a separating layer of various polyimide or other structures. Example 40 utilizes "MATRIMID" 5218 as the separating layer and "ULTEM" 1000, a polyetherimide made by GE as substrate. Its selectivity was measured with $O_2/N_2$ mixtures.

U.S. Pat. No. 5,042,992 discloses a novel class of polyimides based on a partially fluorinated polyimide. It is said to be useful for making semipermeable membranes which have a high permeability and acceptable selectivity for $CO_2$ from mixtures of $CO_2$ and methane. The examples used to determine selectivity were either made using pure $CO_2$ and methane, a mixture of 30% $CO_2$ and 70% methane, or of 10% $CO_2$ and 90% methane.

U.S. Pat. No. 5,120,329 discloses a method for providing a controlled atmosphere in a food storage facility using a semipermeable membrane which has a higher permeability to $CO_2$ than to nitrogen. Typical $CO_2$ levels are given as about 0 to 20%, with 2% $CO_2$ used as the dividing line between low and high concentrations for various applications. Polyimide membranes are cited as examples of suitable membranes for this application.

In an article by Schell et al, "Membranes can Efficiently Separate $CO_2$ from Mixtures", Oil & Gas Journal, Aug. 15, 1983, page 83, an example is given of removing low concentrations of $CO_2$ from a refinery off-gas containing hydrogen by using a commercially available but unspecified membrane that allows $CO_2$ to permeate more rapidly than hydrogen. A two-stage membrane system was required to reduce the $CO_2$ concentration from 6% to 0.2% (60,000 ppm to 2000 ppm), with 50% of the hydrogen still retained in the non-permeate stream.

The problems inherent in removing low concentrations of impurities by gas permeation techniques are discussed in some detail in the Membrane Handbook, written by W. S. Winston Ho and K. K. Sirkar, published by Van Nostrand Reinhold, 1992. On pages 22 and 23 of this reference, it is noted that an externally applied field such as an electrical or magnetic field may be used to provide an additional driving force across the membrane for such cases, and states: "This makes it feasible to separate electrochemically gases that have a low feed concentration. Carbon dioxide, oxygen, and sulfur oxides have been separated in the laboratory by this technique." This laboratory method of removing low concentrations of $CO_2$ has the disadvantage of requiring special equipment which would be expensive and not easily available on a commercial scale.

SUMMARY OF THE INVENTION

In accordance with the invention, a process is provided for removing carbon dioxide from a fluorocarbon carbon dioxide mixture in which the fluorocarbon carbon dioxide mixture is contacted with a semipermeable membrane to form at least one exit stream having an increased concentration of carbon dioxide and at least one exit stream having a reduced concentration of carbon dioxide.

In a preferred form of the invention, the fluorocarbon in the fluorocarbon carbon dioxide mixture consists essentially of non-chlorine containing fluorocarbons. It is also preferred for the fluorocarbon to have at most one hydrogen atom. More preferably, the fluorocarbon carbon dioxide mixture contains a fluorocarbon selected from the group consisting of trifluoromethane (HFC-23), hexafluoroethane (FC-116), tetrafluoroethylene (TFE), hexafluoropropylene (HFP), perfluoro(alkyl vinyl ethers) (PAVE) wherein the alkyl group contains 1–3 carbon atoms, and hexafluoropropylene oxide (HFPO). A particularly preferred fluorocarbon is tetrafluoroethylene.

In a preferred form of the invention, the semipermeable membrane is a polyimide membrane having phenylindane residues incorporated in the polyimide backbone chain. In another preferred mode, the semipermeable membrane is a polyaramid membrane.

The invention is advantageously used to remove low quantities of $CO_2$, i.e., less than 3 weight % carbon dioxide being present in the fluorocarbon carbon dioxide mixture. The invention is also advantageously used to remove trace quantities of $CO_2$, i.e., less than 0.1 weight % carbon dioxide being present in the fluorocarbon carbon dioxide mixture.

In a preferred form of the invention, the exit stream with increased concentration of carbon dioxide contains less than about 10% by weight of the fluorocarbon present in the original fluorocarbon carbon dioxide mixture.

DETAILED DESCRIPTION

Figure 1:
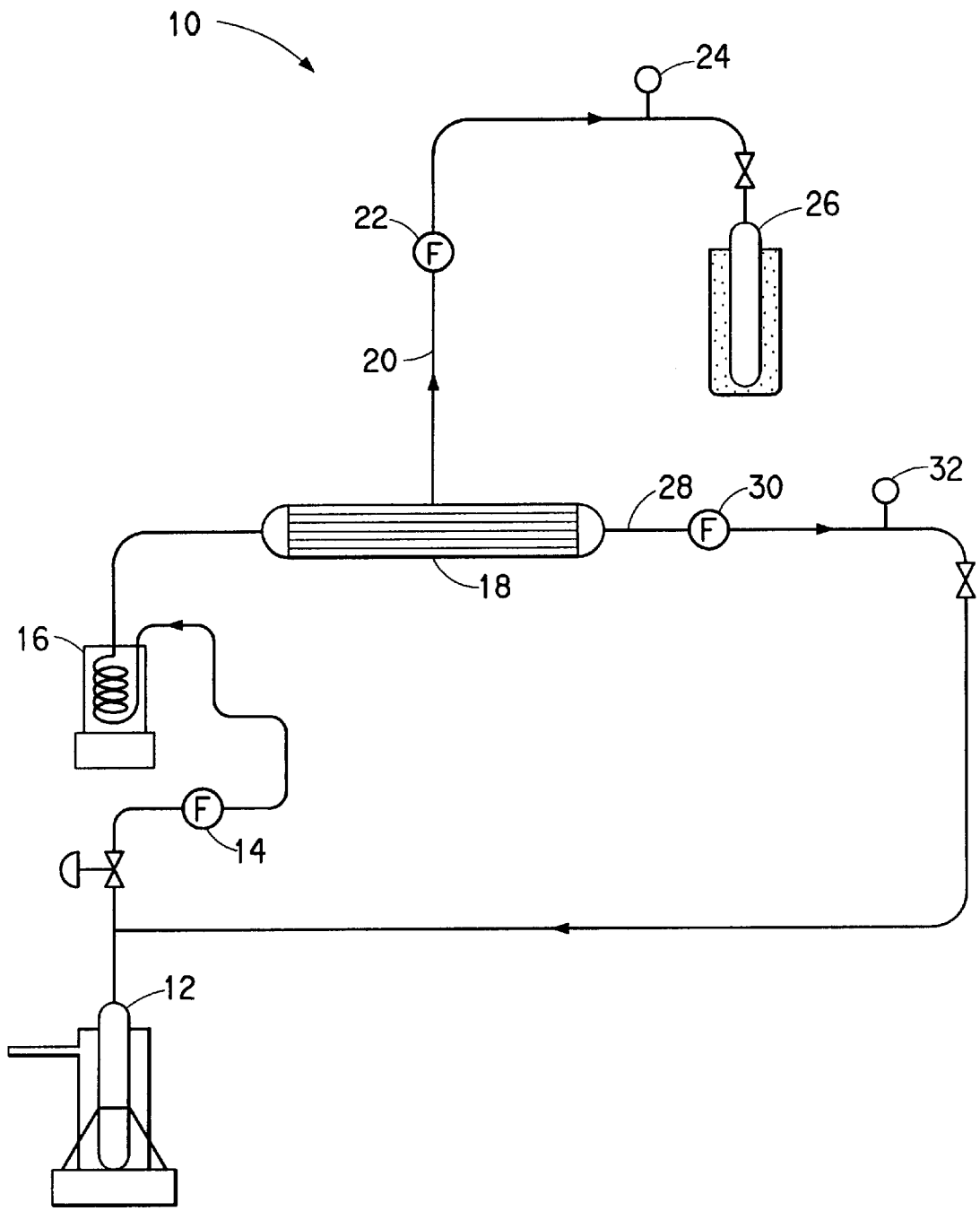
FIG. 1 is a diagrammatical view of laboratory scale apparatus illustrating an embodiment of the present invention.

In the context of the present invention, "fluorocarbon" means an organic compound containing carbon and fluorine. Fluorocarbons in the fluorocarbon carbon dioxide mixture for the practice of the present invention may also contain hydrogen, oxygen and/or other halogens. Preferably, the fluorocarbon consists essentially of non-chlorine containing fluorocarbons. "Consisting essentially of non-chlorine containing fluorocarbons" means that the chlorine content from chlorinated impurities of the starting fluorocarbon carbon dioxide mixture is less than about 0.1 weight %. Preferably, in addition, the fluorocarbon contains at most one hydrogen atom per molecule. More preferably, the fluorocarbon is selected from the group consisting of trifluoromethane (HFC-23), hexafluoroethane (FC-116), tetrafluoroethylene (TFE), hexafluoropropylene (HFP), perfluoro(alkyl vinyl ethers) (PAVE) wherein the alkyl group contains 1–3 carbon atoms, and hexafluoropropylene oxide (HFPO). A particularly preferred fluorocarbon is tetrafluoroethylene.

The fluorocarbon component of the fluorocarbon carbon dioxide mixture from which $CO_2$ is removed by the process of the present invention is comprised of at least one fluorocarbon compound. Thus, the fluorocarbon component of the fluorocarbon carbon dioxide mixture can be a mixture of fluorocarbon compounds. Such mixtures include, for example, HFP/HFPO, TFE/IHFP, TFE/PAVE, and TFE/HFP/PAVE. In the foregoing mixtures, PAVE can be a single compound or a PAVE mixture, e.g., a mixture of perfluoro (methyl vinyl ether) and perfluoro(propyl vinyl ether), or, e.g., a mixture of perfluoro(ethyl vinyl ether) and perfluoro (propyl vinyl ether). One skilled in the art will recognize that compounds other than those defined above (chlorine-free, at most one hydrogen) can be present in the mixture. Such other compounds can contain fluorine or can be fluorine-free, and may or may not be separated from $CO_2$ by the process of the present invention.

The invention is advantageously applied to process streams which contain low quantities of $CO_2$. By "low quantities of $CO_2$" is meant quantities below about 3 weight %. The invention is also advantageously applied to process streams which contain trace quantities of $CO_2$. By "trace quantities of $CO_2$" is meant quantities less than about 0.1 weight %, i.e., less than about 1000 parts per million (ppm) on a weight basis.

In the present process, the fluorocarbon gas containing $CO_2$ is contacted with a selected semipermeable membrane to form two exit streams, one of which is fluorocarbon depleted in $CO_2$ and the other is fluorocarbon enriched in $CO_2$. Usually, the reduced $CO_2$ stream is the "non-permeate" stream, often called the "reject" stream, and does not pass through the membranes whereas the "permeate" stream passes through the membrane and has increased $CO_2$ content. Typically, the stream with reduced $CO_2$ content is recovered, i.e., shipped or sold in the form recovered, processed by contact with other semipermeable membranes, or farther processed by conventional means to achieve additional separation or recovery/removal of a desired component. The fluorocarbon enriched in $CO_2$ can be recycled to earlier stages in the purification process, subjected to further purification before recycling, blended with fluorocarbon used for less demanding markets, or disposed of by incineration or other means as permitted by environmental regulations. The process of the invention can also be used to obtain purified fluorinated compounds from mixtures with $CO_2$ such as the $TFE/CO_2$ shipping mixture disclosed in U.S. Pat. No. 5,345,013. Other components, organic or inorganic, may be present during the contacting step of the instant invention.

The membrane separation device useful in the present invention can be any such device as known in the art and may be in any shape which has a feed side and a permeate side. Included in this description are membranes which can be formed into films (with or without support), tubular devices, spiral wound devices, hollow fibers and the like.

The semipermeable membrane useful in the instant invention preferably is polyimide membrane or polyaramid membrane. Such membrane may be made of any polyimide or polyaramid material capable of preferentially passing the $CO_2$ relative to the fluorocarbon. That is, the ratio of permeation rates of the $CO_2$ to that of the fluorocarbon should be greater than 1. Obviously, the higher the ratio, the more efficient will be the separation process.

Polyimide membranes typically used in commercial use for conventional gas separations may be used. Preferably, the polyimide has phenylindane residues incorporated in the polyimide backbone chain. One membrane of this type is "MATRIMID" 5218 polyimide resin, manufactured by Ciba-Geigy and based on 5(6)-amino-1-(4'-aminophenyl)-1,3-trimethylindane. The membrane may be a composite of a porous substrate and the polyimide resin. For example, hollow fibers of "Ultem" 1000, a polyetherimide made by General Electric, are a particularly suitable support for "Matrimid" 5218. Such membranes and their manufacture are described in U.S. Pat. No. 5,085,676. Polyaramid membranes that can be used include those of the types disclosed in U.S. Pat. No. 5,085,774.

As in known permeation separation process, parameters which are usually considered as variables to enhance the separation process are the temperature, the pressure differential and pressure ratio between the feed side of the membrane and the permeate side of the membrane, and the residence time of the feed stream on the feed side of the membrane and the residence time of the permeate on the permeate side of the membrane. In the instant invention, these parameters may be varied to enhance the separation so long as the values selected are not damaging to the membrane material. Temperature can be any convenient temperature, usually from about −50 to 150° C. The primary temperature limitations are that the temperature should be below any temperature at which the membrane is affected adversely and above the dew point of the fluorocarbon. Preferably, the temperature range will be from about 0 to about 75° C.

The pressure differential between the feed side of the membrane and the permeate side is preferably at least about 0.1 atmosphere (10 kPa). The process may be operated at a lesser pressure differential but the separation process will be slower. The pressure differential can be the result of higher pressure on the feed side of the semipermeable membrane or the result of reduced pressure on the permeate side of the membrane or a combination of both. Useful feed pressures can vary substantially with the mode in which the membrane device is employed and with the materials being separated. For hollow fiber membranes, for example, feed pressure might be as high as 1000 psig (7 MPa) for feed to the outside of the fibers (shell-side feed) but might be limited to 200–250 psig (1.5–1.8 MPa) for bore-side feed. Additionally, choice of pressure should be consistent with safe handling of the various streams.

The present process can be carried out as a batch process or as a continuous process. Since this permeation separation process is a differential process producing a substantial reduction in $CO_2$, multiple pass or multiple stage processes may be the most efficient system to achieve very high purity fluorocarbons. In such multiple stage arrangements, an output stream from one stage can be fed to another stage either as the primary feed to that other stage or as a recycle stream. The term "stage" as used in the present application is intended to encompass a stage in which gases are fed to a separate membrane separation device or a pass in which gases are returned to the same device. When low or trace levels of $CO_2$ are present, removal to a few ppm can be achieved in a one or two stage process. Preferably, at least about 50%, more preferably at least about 75%, by weight of the $CO_2$ present is removed in each stage. The present invention provides separation without the purchase and addition of extraneous materials and without creating additional waste disposal problems.

Preferred processes in accordance with the invention can provide low "losses" of the fluorocarbon. "Loss" is determined from the weight of the fluorocarbon in the stream with increased carbon dioxide concentration (usually the permeate stream) in relation to the weight of the fluorocarbon present in the original fluorocarbon carbon dioxide mixture. Preferably, the exit stream with increased concentration of carbon dioxide contains less than about 10% by weight, more preferably less than about 5 percent, and most preferably less than about 2%, of the fluorocarbon present in the original fluorocarbon carbon dioxide mixture. The aforesaid low losses can be achieved in multiple stage processes, but preferably are achieved in a single stage.

The following examples are presented for illustrative purposes only and in no way are intended to limit the present inventive process.

EXAMPLE 1

This example illustrates the invention for removal of $CO_2$ from a mixture of HFC-23 and $CO_2$.

With reference to FIG. 1 illustrating laboratory scale apparatus 10 for carrying out the present invention, a 1 kg mixture of HFC-23 containing 1.11 weight % $CO_2$ is placed in a pressure cylinder 12 at 25° C. and about 200 psig (1400 kPa). The pressure cylinder 12 is connected to a flow meter 14 and then to a hot water heated coil 16 to adjust the temperature of the HFC-23 mixture. After leaving the coil 16, the gases enter the inlet side of a permeation separator 18 with a commercial polyimide membrane in the form of 360 hollow fibers 73 cm long having outside diameter of 160 $\mu$m and bore diameter of 90 $\mu$m. The membrane used is Ciba Geigy's "MATRIMID" 5218 polyimide skin covering a bulk porous fiber wall made of General Electric's "ULTEM" 1000. The permeate gas is fed via line 20 to a flowmeter 22 and vacuum pump 24 to collection cylinder 26. The non-permeate gas or product is fed via line 28 to a flowmeter 30 and to a vacuum pump 32 for recycling back to the line from feed cylinder 12. Thus, the feed concentration changes from the original value of 1.11 weight % $CO_2$ to very low values during the course of the test, permitting us to evaluate the separation system under a variety of inlet feed concentrations. Under conditions of the test, the feed pressure into the permeator is initially about 120 psig (930 kPa) and the pressure at the non-permeate discharge is about 110 psig (860 kPa). While these pressures drop slightly during the course of the test, the pressure differential of 10 psig (170 kPa) is maintained throughout the test. The permeate pressure at the vacuum pump is maintained at about 0.5 psia (3 kPa) during the test. However, when drawing off permeate samples, the vacuum pump is turned off for a few minutes, allowing pressure to build up to about 5 psia (35 kPa) to permit a sample to be taken, after which the test is resumed under the original 0.5 psia (3 kPa) pressure.

Figure 2:
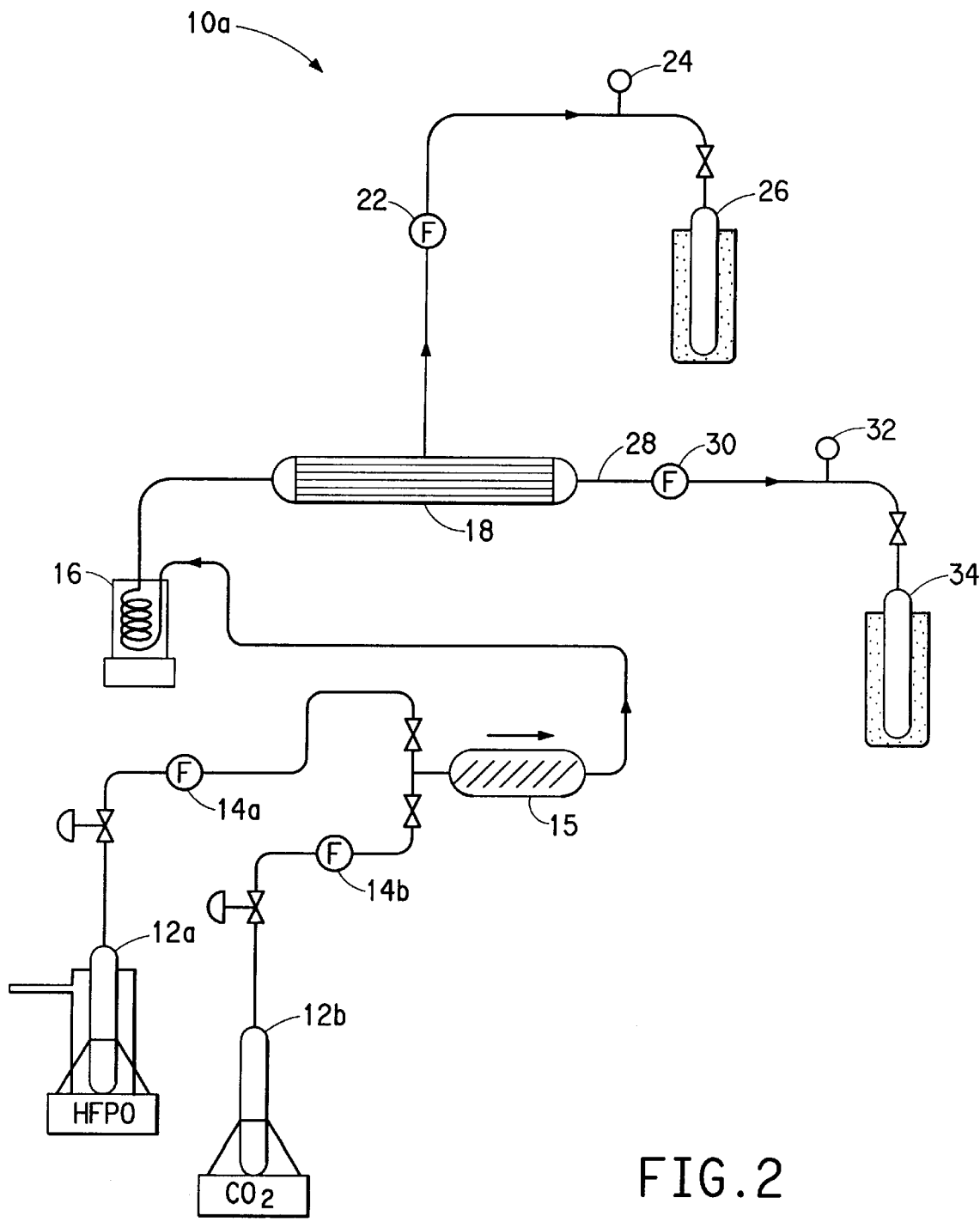
FIG. 2 is a diagrammatical view of alternate laboratory scale apparatus illustrating an embodiment of the present invention.

Permeate sample analyses are checked against the calculated values obtained by mass balance calculations from flow measurements and the analyses of feed and non-permeate analyses as shown in FIG. 2, and found to be in reasonably good agreement. The permeate concentrations found by analysis are all slightly lower than the mass balance values, perhaps because of the momentarily higher permeate pressures during sampling. Samples are analyzed by gas chromatograph using a POREPAK-T column. Flow-rates are measured with a Hastings transducer, with results corrected to standard temperature and pressure (STP) for the specific gases used.

In Table 1 below, flowrates are given in liters/minute at STP, and concentrations of $CO_2$ in HFC-23 given in parts per million (ppm) by volume. The $CO_2$ concentrations given for the permeate gas are those calculated from the mass balance data, since permeate samples are not taken every time period.

TABLE 1

| Time | Flowrates (Liter/min.) | | | Feed Pressure | $CO_2$ Concentr. (ppm by vol.) | | |
|---|---|---|---|---|---|---|---|
| Hrs. | Feed | Perm. | Non-Perm. | kpa | Feed | Permeate | Product |
| 0.50 | 1.066 | 0.292 | 0.763 | 930 | 17,517 | 63,941 | 16.4 |
| 1.50 | 1.066 | 0.268 | 0.736 | 930 | 16,338 | 64,964 | 21.3 |
| 2.25 | 1.244 | 0.259 | 0.899 | 930 | 14,249 | 68,265 | 59.2 |
| 3.25 | 1.244 | 0.246 | 0.954 | 930 | 11,431 | 57,524 | 79.6 |
| 5.75 | 1.096 | 0.208 | 0.872 | 930 | 7,000 | 36,749 | 35.0 |
| 7.00 | 0.859 | 0.213 | 0.681 | 930 | 4,322 | 17,378 | 16.4 |
| 10.25 | 1.155 | 0.155 | 0.954 | 840 | 2,218 | 16,351 | 30.6 |
| 11.50 | 1.096 | 0.143 | 0.899 | 805 | 1,530 | 11,521 | 33.5 |
| 12.25 | 0.770 | 0.130 | 0.627 | 710 | 1,049 | 6,171 | 9.1 |
| 14.25 | 0.710 | 0.115 | 0.627 | 680 | 714 | 4,401 | 2.3 |
| 14.75 | 0.710 | 0.111 | 0.627 | 620 | 589 | 3,681 | 16.2 |
| 17.50 | 0.651 | 0.091 | 0.627 | 600 | 483 | 3,388 | 10.3 |
| 18.25 | 0.651 | 0.081 | 0.627 | 565 | 261 | 2,082 | 2.3 |
| 19.00 | 0.533 | 0.080 | 0.517 | 570 | 126 | 830 | 1.4 |
| 21.00 | 0.533 | 0.068 | 0.517 | 495 | 105 | 816 | 1.0 |

Although there is some variation in results for individual time periods, the general results may be divided into clear groups, as shown by the horizontal lines in the table above. When the initial concentration of $CO_2$ in the HFC-23 range from about 11,400 to 17,500 ppm by volume (7,200 to 11,100 ppm by weight), the purified product (the non-permeate) has a $CO_2$ content ranging from only 16 to 80 ppm by volume (10 to 50 ppm by weight). With a feed concentration of 1,100 to 7,000 ppm $CO_2$ by volume in HFC-23 (600 to 4,400 ppm by weight), the purified product has a $CO_2$ content ranging from 9 to 35 ppm by volume (6 to 22 ppm by weight). With a feed concentration of 110 to 710 ppm $CO_2$ by volume in HFC-23 (70 to 400 ppm by weight), the purified product has a $CO_2$ content ranging from 1 to 16 ppm by volume (0.6 to 10 ppm by weight).

The above results show that HFC-23 with a $CO_2$ content of up to about 1.2 weight % can be reduced in $CO_2$ content to a few ppm by one or two passes through a polyimide membrane separator, depending in part on the size/residence time of the separators, the exact process conditions, the desired recovery rate for HFC-23, and the future treatment of the permeate gas (HFC-23 with a high percent of $CO_2$).

EXAMPLE 2

This example illustrates removing $CO_2$ from a mixture of HFPO and $CO_2$.

As illustrated in FIG. 2, apparatus 10a is the apparatus of Example 1 but modified by adding separate feed cylinders 12a and 12b and feed lines controlled by flowmeters 14a and 14b for each of the two components, $CO_2$ and HFPO respectively. A packed cylinder 15 is also added for thorough mixing. After calibration, the mass flow units are set to give a combined composition of 1.2 weight % of $CO_2$ in a mixture with HFPO. As in Example 1, the mixture of gases is connected to the inlet side of the same permeation separator 18. The permeate $CO_2$ gas is captured by direct reaction with $NH_3$ in cylinder 26. The non-permeate HFPO product is captured by dry ice condensation in cylinder 34 which is added in place of the recycle of the apparatus of FIG. 1. The test is conducted for 3.5 hours. For the first 10 minutes, a feed pressure of 100 psig (700 kPa) is used, but some signs of HFPO condensation and erratic flow are noted. This is eliminated by dropping the feed pressure to 90 psig (620 kPa) and adding supplemental HFPO heating.

Weight changes on the feed tanks, corrected for the amount of material required to fill the system, showed a total feed of 298.0 g of HFPO and 5.0 gm of $CO_2$, for an average feed composition of 1.6 weight % $CO_2$. The permeate captured is 2.6 g, and the non-permeate captured is 290.0 g, for an overall mass balance (feed vs recovery) of 96.6%. Colorimetric tests are carried out on the products, based on the observation that the $CO_2/NH_3$ reaction product stays water clear with time, while the $HFPO/NH_3$ reaction product darkens in minutes to faint yellow, and then to dark yellow, red/orange and eventually black over a 24 hour period. These tests indicate that the permeate is essentially all $CO_2$, with less than 1% HFPO, and that the non-permeate is HFPO with about 0.8 weight % $CO_2$, about a 50% reduction. Direct infra-red measurements indicate that the $CO_2$ content of the non-permeate is below 0.1 weight %, an even greater reduction in $CO_2$ content.

EXAMPLE 3

This example illustrates removing $CO_2$ from a mixture of HFPO and $CO_2$ using collection of the permeate by liquid nitrogen condensation.

The apparatus used in Example 2 is modified to collect the permeate in cylinder 26 by liquid nitrogen condensation, enabling the permeate side of the membrane to operate under vacuum. Improved results are noted compared to Example 2, presumably due to operation under reduced pressure. The $CO_2$ in the feed is estimated to be about 3.0 weight %. The $CO_2$ in the permeate is again estimated at above 99 weight %. By calorimetric analysis, the $CO_2$ in the non-permeate product is estimated at about 0.6 weight %, for an approximate 80% reduction in $CO_2$ content with negligible HFPO loss. Direct infra-red measurements indicate that the $CO_2$ content of the non-permeate is below 0.1 weight %, an even greater reduction in $CO_2$ content.

EXAMPLE 4

A permeator similar to that of Example 1 except that fiber length is 41 cm is used to separate a mixture of 48 wt % TFE and 52 wt % $CO_2$ at 23°±2° C. The experimental arrangement differs from that shown in FIG. 1. With reference to FIG. 1, the $TFE/CO_2$ source 12 is a cylinder initially charged with 3800 g of the gas mixture at 420 psig (3.0 MPa) and recharged only as necessary. The cylinder is equipped with a pressure regulator set to deliver the feed gas at 60 psig (0.52 MPa). A GC sample is taken between the mass flow meter 14 and the permeator 18. The heated coil 16 is not used. On the reject (i.e., non-permeate) side, the exit pressure is controlled by a throttle valve to create a range of feed-side pressure differences, Δp. The reject stream passes through volumetric flow meter 30 to atmospheric pressure. Vacuum pump 32 and the recycle line to the feed cylinder 12 are not used. On the permeate side, the permeate passes through volumetric flow meter 22 to atmospheric pressure. Vacuum pump 24 collection cylinder 26 are not used. GC samples are taken in both the permeate and reject streams upstream from the flow meters. The combined flow and GC measurements lead to a good mass balance, enhancing confidence in the flow and GC data. Flow rate and compositional data summarized in Table 2 show that a $TFE/CO_2$ stream rich in $CO_2$ can be separated effectively with a polyimide membrane. "Loss" is the fraction (%) of total TFE flow that is in the permeate stream. There is no evidence of reaction between the membrane and the highly reactive TFE. I.e., there is no evidence of attack of the membrane by the TFE, and no evidence of TFE polymerization which is known in $CO_2$ media (no initiation by the membrane).

TABLE 2

Separation of TFE and $CO_2$ with Polyimide Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 59.0 | 407 | 8.604 | 60.0 | 0.0520 | 0.60 |
| 25.0 | 172 | 5.233 | 71.4 | 0.0786 | 1.48 |
| 12.8 | 88 | 3.912 | 82.7 | 0.0967 | 2.41 |
| 5.6 | 39 | 1.977 | 91.2 | 0.1046 | 5.02 |
| 2.7 | 19 | 0.960 | 95.8 | 0.1225 | 11.3 |
| 1.1 | 8 | 0.334 | 98.5 | 0.1204 | 26.5 |

EXAMPLE 5

The procedure of Example 4 is essentially repeated, except that a permeator made with polyaramid hollow fibers is used and feed pressure values of 100 and 145 psig (0.79 and 1.10 MPa) are tested in addition to 60 psig. The fiber membranes are made generally according to Examples 9–12 of U.S. Pat. No. 5,085,774 and the permeator incorporates 200 such fibers 73 cm long having outside diameter of 200 μm and bore diameter of 80 μm. Flow rate and compositional data summarized in Tables 3–5 show that a $TFE/CO_2$ stream rich in $CO_2$ can be separated effectively with a polyaramid membrane. Note, in comparison with Example 4, that polyaramid provides less "loss" at a given purity but has lower productivity despite higher membrane area. However, productivity can be enhanced by increased feed pressure without significant impact on loss. There is no evidence of reaction between the membrane and the highly reactive TFE. I.e., there is no evidence of attack of the membrane by the TFE, and no evidence of TFE polymerization which is known in $CO_2$ media (no initiation by the membrane).

TABLE 3

$TFE/CO_2$ Separation at 60 psig with Polyaramid Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 4.8 | 33 | 0.3409 | 56.0 | 0.00068 | 0.20 |
| 2.8 | 19 | 0.2140 | 60.7 | 0.00071 | 0.33 |
| 1.8 | 12 | 0.1440 | 66.0 | 0.00069 | 0.48 |
| 1.0 | 7 | 0.0937 | 78.9 | 0.00079 | 0.83 |
| 0.5 | 3 | 0.0559 | 85.5 | 0.00073 | 1.29 |

TABLE 4

$TFE/CO_2$ Separation at 100 psig with Polyaramid Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 4.9 | 34 | 0.5435 | 58.1 | 0.00110 | 0.20 |
| 3.7 | 23 | 0.4318 | 60.5 | 0.00112 | 0.26 |
| 2.7 | 19 | 0.3358 | 63.6 | 0.00120 | 0.36 |
| 1.8 | 12 | 0.2532 | 69.7 | 0.00123 | 0.48 |
| 0.8 | 6 | 0.1398 | 82.1 | 0.00137 | 0.97 |
| 0.5 | 3 | 0.0972 | 90.2 | 0.00149 | 1.51 |

TABLE 5

TFE/CO$_2$ Separation at 145 psig with Polyaramid Membrane

| Δp | | TFE in Reject Stream | | TFE in Permeate Stream | |
|---|---|---|---|---|---|
| (psi) | (kPa) | Rate (g/min) | Purity (wt %) | Rate (g/min) | Loss (%) |
| 5.1 | 35 | 0.8438 | 59.9 | 0.00192 | 0.23 |
| 4.2 | 29 | 0.7101 | 62.2 | 0.00196 | 0.27 |
| 3.2 | 22 | 0.5777 | 65.7 | 0.00196 | 0.34 |
| 2.0 | 14 | 0.4086 | 72.9 | 0.00210 | 0.51 |
| 1.0 | 7 | 0.2393 | 84.0 | 0.00233 | 0.96 |
| 0.5 | 3 | 0.1509 | 89.8 | 0.00227 | 1.49 |

EXAMPLE 6

This example illustrates separation of TFE and CO$_2$ using a two-stage permeator setup. Two permeators similar to that described in Example 4 are arranged in series, with the reject stream from the first permeator being the feed stream to the second permeator. Feed pressures $p_1$ to stage 1 of 60, 100 and 140 psig (0.52, 0.79, and 1.07 MPa) are tested at various total Δp with Δp regulated so that $Δp_1=2Δp_2$, wherein the subscripts identify the stage. Tables 6 and 7 show data for total Δp of 6 and 12 psi (41 and 83 kPa). Note that total "loss" can be limited to first-stage "loss" by recycling second-stage permeate with appropriate pressure increase to the first-stage feed, which is especially convenient when the second-stage permeate composition is close to that of the first-stage feed.

TABLE 6

Data for Stage 1 of Example 6

| $p_1$ | $Δp_1$ | TFE in Reject Stream | | TFE in Permeate Stream | |
|---|---|---|---|---|---|
| (MPa) | (kPa) | Rate (g/min) | Purity (wt %) | Rate (g/min) | Loss (%) |
| 0.52 | 27.6 | 1.078 | 87.2 | 0.0333 | 2.99 |
| 0.52 | 55.2 | 2.073 | 75.1 | 0.0350 | 1.66 |
| 0.79 | 27.6 | 2.121 | 88.9 | 0.0678 | 3.10 |
| 0.79 | 55.2 | 3.563 | 78.0 | 0.0544 | 1.50 |
| 1.07 | 27.6 | 2.082 | 94.7 | 0.1256 | 5.69 |
| 1.07 | 55.2 | 4.778 | 82.4 | 0.1043 | 2.14 |

TABLE 7

Data for Stage 2 of Example 6

| $P_2$ | $ΔP_2$ | Stream TFE in Reject Stream | TFE in Permeate Stream | | |
|---|---|---|---|---|---|
| (MPa) | (kPa) | Reject | Permeate | Rate (g/min) | Loss (%) |
| 0.49 | 13.8 | 89.3 | 22.5 | 0.0072 | 0.67 |
| 0.46 | 27.6 | 81.4 | 4.2 | 0.0063 | 0.30 |
| 0.77 | 13.8 | 92.6 | 18.0 | 0.0152 | 0.71 |
| 0.74 | 27.6 | 85.3 | 3.7 | 0.0127 | 0.36 |
| 1.04 | 13.8 | 95.9 | 45.2 | 0.0248 | 1.19 |
| 1.01 | 27.6 | 90.1 | 5.7 | 0.0248 | 0.53 |

EXAMPLE 7

The experimental arrangement of Example 6 is used to generate a feed stream to the second-stage permeator that is low in CO$_2$. This is done by feeding a TFE/CO$_2$ mixture containing 50.3 wt % of CO$_2$ to the first stage at 180 psig (1.34 MPa), using low $Δp_1$ of 1.0 and 0.8 psi (6.9 and 5.5 kPa), and using reduced pressure (partial vacuum) on the permeate side of the first stage permeator. The resulting streams containing 2.96 and 1.14 wt % of CO$_2$, respectively, are processed through the second-stage permeator at $Δp_2$ of 0.5 psi (3.4 kPa). Data in Table 8 show that the process of this invention can be used effectively to separate TFE and CO$_2$ even when the CO$_2$ concentration is low to obtain TFE of even higher purity.

TABLE 8

Polyimide Membrane at Low CO$_2$ Concentration (Example 7)

| CO$_2$ Conc. (wt %) | | TFE Rate (g/min) | | CO$_2$ Rate (g/min) | | Removed |
|---|---|---|---|---|---|---|
| Feed | Reject | Feed | Reject | Feed | Reject | CO$_2$ (%) |
| 2.96 | 1.03 | 1.589 | 1.582 | 0.0485 | 0.0165 | 66.0 |
| 1.14 | 0.58 | 1.172 | 1.148 | 0.0135 | 0.0067 | 50.4 |

What is claimed is:

1. A process for removing carbon dioxide from a fluorocarbon carbon dioxide mixture comprising one or more stages in which a feed stream of said fluorocarbon carbon dioxide mixture is contacted with a semipermeable membrane to form at least one exit stream having an increased concentration of carbon dioxide and at least one exit stream having a reduced concentration of carbon dioxide, said process in at least one of said one or more stages causing said exit stream with increased concentration of carbon dioxide to contain less than about 5% by weight of the fluorocarbon present in said feed stream.

2. The process of claim 1 wherein said fluorocarbon of said fluorocarbon carbon dioxide mixture consists essentially of non-chlorine containing fluorocarbons.

3. The process of claim 1 wherein said fluorocarbon has at most one hydrogen atom.

4. The process of claim 1 wherein said fluorocarbon carbon dioxide mixture comprises a fluorocarbon selected from the group consisting of trifluoromethane (HFC-23), hexafluoroethane (FC-116), tetrafluoroethylene, hexafluoropropylene, perfluoro(alkyl vinyl ethers) wherein the alkyl group contains 1–3 carbon atoms, and hexafluoropropylene oxide (HFPO).

5. The process of claim 1 wherein said fluorocarbon comprises tetrafluoroethylene.

6. The process of claim 1 wherein said semipermeable membrane comprises a membrane selected from the group consisting of polyimide membranes and polyaramid membranes.

7. The process of claim 1 in which the semipermeable membrane comprises a polyimide membrane having phenylindane residues incorporated in the polyimide backbone chain.

8. The process of claim 1 wherein less than 3 weight % carbon dioxide is present in said fluorocarbon carbon dioxide mixture.

9. The process of claim 1 wherein less than 0.1 weight % carbon dioxide is present in said fluorocarbon carbon dioxide mixture.

10. The process of claim 1 wherein said process in at least one stage causes at least 50% by weight of said carbon dioxide present in said feed stream to be removed in said stage.

11. The process of claim 1 wherein said exit stream with increased concentration of carbon dioxide contain less than about 10% by weight of the fluorocarbon present in said fluorocarbon carbon dioxide mixture prior to said contacting with said semipermeable membrane.

12. The process of claim 1 wherein said exit stream with increased concentration of carbon dioxide contain less than about 5% by weight of the fluorocarbon present in said fluorocarbon carbon dioxide mixture prior to said contacting with said semipermeable membrane.

* * * * *